US012664681B2

(12) United States Patent
Kusu et al.

(10) Patent No.: US 12,664,681 B2
(45) Date of Patent: Jun. 23, 2026

(54) PROGRAM FOR DETERMINING DIRECTION OF INTEREST IN INTRAVASCULAR ULTRASOUND MEDICAL IMAGING

(71) Applicant: TERUMO KABUSHIKI KAISHA, Tokyo (JP)

(72) Inventors: Kohtaroh Kusu, Ebina (JP); Yuki Sakaguchi, Fujisawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 320 days.

(21) Appl. No.: 18/470,514

(22) Filed: Sep. 20, 2023

(65) Prior Publication Data

US 2024/0013434 A1 Jan. 11, 2024

Related U.S. Application Data

(63) Continuation of application No. PCT/JP2022/010279, filed on Mar. 9, 2022.

(30) Foreign Application Priority Data

Mar. 24, 2021 (JP) ................................. 2021-050689

(51) Int. Cl.
| | |
|---|---|
| *G06T 7/73* | (2017.01) |
| *G06V 20/50* | (2022.01) |
| *G16H 30/40* | (2018.01) |

(52) U.S. Cl.
CPC ................ *G06T 7/74* (2017.01); *G06V 20/50* (2022.01); *G16H 30/40* (2018.01);
(Continued)

(58) Field of Classification Search
None
See application file for complete search history.

(56) References Cited

U.S. PATENT DOCUMENTS

| | | | |
|---|---|---|---|
| 2009/0005679 A1* | 1/2009 | Dala-Krishna | ........... G06T 7/80 600/437 |
| 2016/0070436 A1 | 3/2016 | Thomas et al. | |

(Continued)

FOREIGN PATENT DOCUMENTS

| | | | |
|---|---|---|---|
| CN | 111161216 A * | 5/2020 | ............. G06N 3/045 |
| JP | 2016517288 A | 6/2016 | |

(Continued)

OTHER PUBLICATIONS

International Search Report (PCT/ISA/210) with English translation and Written Opinion (PCT/ISA/237) mailed on Apr. 26, 2022, by the Japanese Patent Office as the International Searching Authority for International Application No. PCT/JP2022/010279.
(Continued)

*Primary Examiner* — Andrew M Moyer
*Assistant Examiner* — Caroline E. Depalma
(74) *Attorney, Agent, or Firm* — .Buchanan Ingersoll & Rooney PC

(57) ABSTRACT

The program causes a computer to execute processing of: acquiring a medical image obtained by imaging a luminal organ using a catheter; specifying a direction of interest indicating a direction of a site of interest with respect to the medical image on the basis of the acquired medical image; and displaying information indicating the specified direction of interest in association with the medical image or displaying the medical image subjected to image processing on the basis of the information indicating the direction of interest.

19 Claims, 7 Drawing Sheets

(52) U.S. Cl.
CPC .............. *G06T 2207/10101* (2013.01); *G06T 2207/10132* (2013.01); *G06T 2207/30048* (2013.01); *G06T 2207/30101* (2013.01); *G06T 2207/30204* (2013.01); *G06V 2201/031* (2022.01)

(56) References Cited

U.S. PATENT DOCUMENTS

| 2016/0113629 | A1 | 4/2016 | Miyake | |
| 2016/0171711 | A1* | 6/2016 | Gopinath | G06T 5/50 |
| | | | | 382/130 |
| 2019/0021694 | A1 | 1/2019 | Sakaguchi | |

FOREIGN PATENT DOCUMENTS

| JP | 2017158892 | A | 9/2017 |
| JP | 2017537768 | A | 12/2017 |
| WO | 2016031273 | A1 | 3/2016 |
| WO | 2017164071 | A1 | 9/2017 |

OTHER PUBLICATIONS

English Translations of the International Search Report (Form PCT/ISA/210) and the Written Opinion of the International Searching Authority (Form PCT/ISA/237) issued Apr. 26, 2022, by the Japan Patent Office in corresponding International Application No. PCT/JP2022/010279. (6 pages).

* cited by examiner

Figure 4:
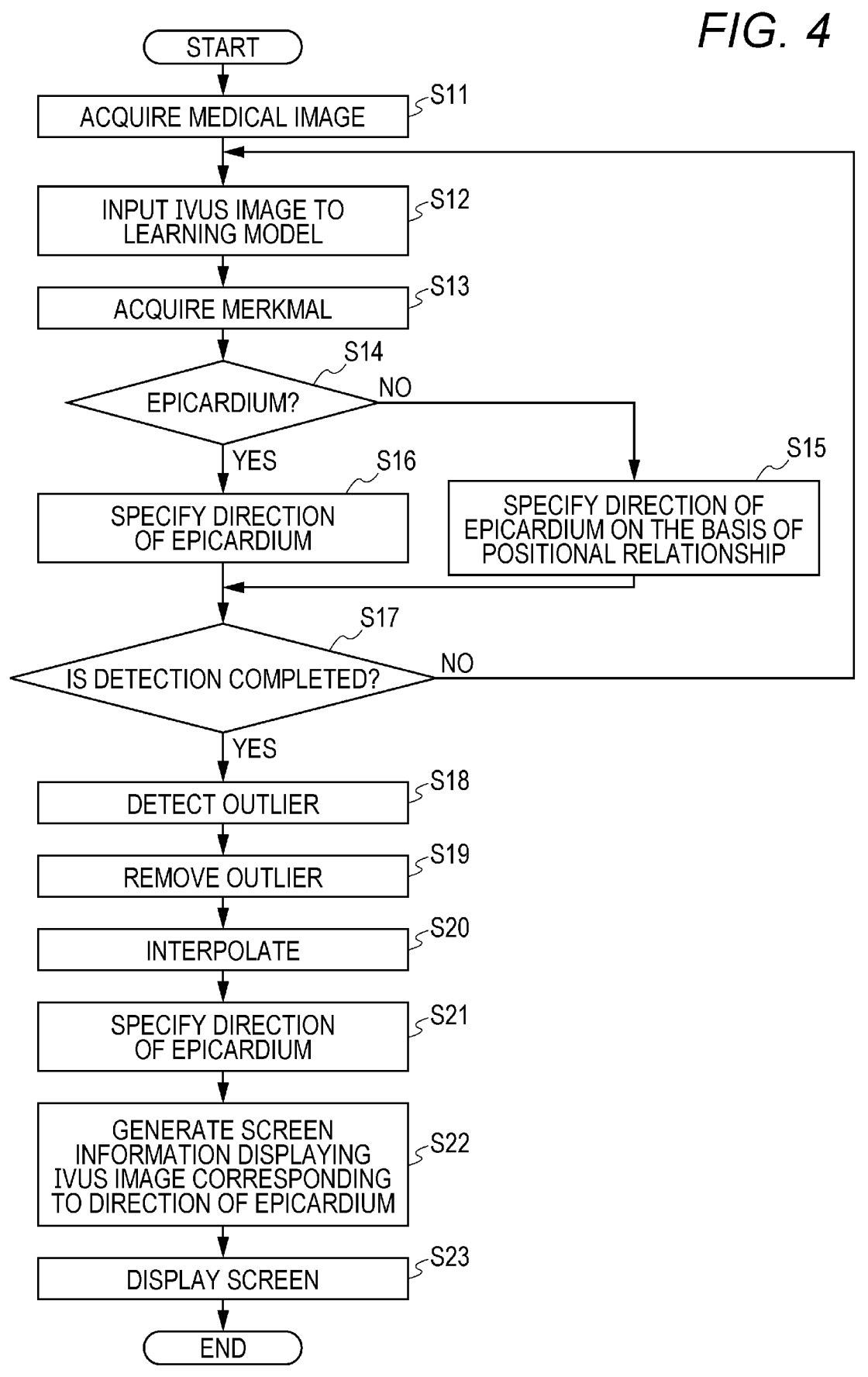

```
              ( START )
                 │
                 ▼
      ┌──────────────────────┐  S11
      │ ACQUIRE MEDICAL IMAGE│
      └──────────────────────┘
                 │ ◄──────────────────────────────────────┐
                 ▼                                         │
      ┌──────────────────────┐  S12                        │
      │   INPUT IVUS IMAGE TO │                            │
      │    LEARNING MODEL     │                            │
      └──────────────────────┘                            │
                 │                                         │
                 ▼                                         │
      ┌──────────────────────┐  S13                        │
      │    ACQUIRE MERKMAL    │                            │
      └──────────────────────┘                            │
                 │           S14                           │
                 ▼                                         │
            ╱─────────╲          NO                        │
           ╱ EPICARDIUM?╲──────────────┐                   │
            ╲─────────╱                │                   │
                 │ YES     S16         ▼      S15          │
                 ▼              ┌───────────────────────┐  │
      ┌──────────────────────┐  │  SPECIFY DIRECTION OF │  │
      │   SPECIFY DIRECTION  │  │ EPICARDIUM ON THE BASIS│  │
      │    OF EPICARDIUM     │  │ OF POSITIONAL          │  │
      └──────────────────────┘  │ RELATIONSHIP          │  │
                 │ ◄────────────└───────────────────────┘  │
                 ▼           S17                           │
            ╱───────────────────╲    NO                    │
           ╱ IS DETECTION COMPLETED?╲──────────────────────┘
            ╲───────────────────╱
                 │ YES
                 ▼
      ┌──────────────────────┐  S18
      │    DETECT OUTLIER     │
      └──────────────────────┘
                 │
                 ▼
      ┌──────────────────────┐  S19
      │    REMOVE OUTLIER     │
      └──────────────────────┘
                 │
                 ▼
      ┌──────────────────────┐  S20
      │     INTERPOLATE       │
      └──────────────────────┘
                 │
                 ▼
      ┌──────────────────────┐  S21
      │   SPECIFY DIRECTION  │
      │    OF EPICARDIUM     │
      └──────────────────────┘
                 │
                 ▼
      ┌──────────────────────┐  S22
      │  GENERATE SCREEN     │
      │ INFORMATION DISPLAYING│
      │ IVUS IMAGE CORRESPONDING│
      │ TO DIRECTION OF EPICARDIUM│
      └──────────────────────┘
                 │
                 ▼
      ┌──────────────────────┐  S23
      │    DISPLAY SCREEN     │
      └──────────────────────┘
                 │
                 ▼
              ( END )
```

< PREVIOUS FRAME                    SUBSEQUENT FRAME >

*FIG. 6*

PROGRAM FOR DETERMINING DIRECTION OF INTEREST IN INTRAVASCULAR ULTRASOUND MEDICAL IMAGING

CROSS-REFERENCES TO RELATED APPLICATIONS

This application is a continuation of International Application No. PCT/JP2022/010279 filed on Mar. 9, 2022, which claims priority to Japanese Application No. 2021-050689 filed on Mar. 24, 2021, the entire content of both of which is incorporated herein by reference.

TECHNOLOGICAL FIELD

The present disclosure generally relates to a program, an information processing method, and an information processing device.

BACKGROUND DISCUSSION

In related art, a catheter for image diagnosis that acquires a medical image in a luminal organ such as a blood vessel using ultrasound waves or light is known, and an image diagnosis apparatus that displays a medical image for image diagnosis generated using such a catheter is disclosed (see, for example, International Patent Application Publication No. WO 2017/164071 A).

A direction of a medical image obtained by an image diagnosis device changes depending on a bending state of a catheter, or the like. It is important for a doctor, or the like, to correctly grasp the direction of the medical image for diagnosis. However, in order to grasp the direction of the medical image, it is necessary to have ability to correctly interpret the drawn medical image, and thus, it is necessary to perform training for a long period.

SUMMARY

A non-transitory computer readable program is disclosed that enables a direction of a medical image to be relatively easily grasped.

A non-transitory computer-readable medium storing a computer program according to an aspect of the present disclosure causes a computer to execute a processing comprising: acquiring a medical image obtained by imaging a luminal organ using a catheter; specifying a direction of interest indicating a direction of a site of interest with respect to the medical image on the basis of the acquired medical image; and displaying information indicating the specified direction of interest in association with the medical image or displaying the medical image subjected to image processing on the basis of the information indicating the direction of interest.

An information processing method according to another aspect of the present disclosure comprising: acquiring a medical image obtained by imaging a luminal organ using a catheter; specifying a direction of interest indicating a direction of a site of interest with respect to the medical image on a basis of the acquired medical image; and displaying information indicating the specified direction of interest in association with the medical image or displaying the medical image subjected to image processing on a basis of the information indicating the direction of interest.

An information processing device according to a further aspect comprising: a control unit configured to: acquire a medical image obtained by imaging a luminal organ using a catheter; specify a direction of interest indicating a direction of a site of interest with respect to the medical image on a basis of the medical image acquired by the acquisition unit; and display information indicating the direction of interest specified by the specification unit in association with the medical image or displays the medical image subjected to image processing on a basis of the information indicating the direction of interest.

According to the present disclosure, it is possible to relatively easily grasp a direction of a medical image.

BRIEF DESCRIPTION OF THE DRAWINGS

FIG. 3 is an explanatory view illustrating outline of a learning model.

FIG. 4 is a flowchart illustrating an example of processing procedure to be executed by the image processing device.

FIG. 6 is an explanatory view for explaining outline of a learning model in a second embodiment.

DETAILED DESCRIPTION

Figure 1:
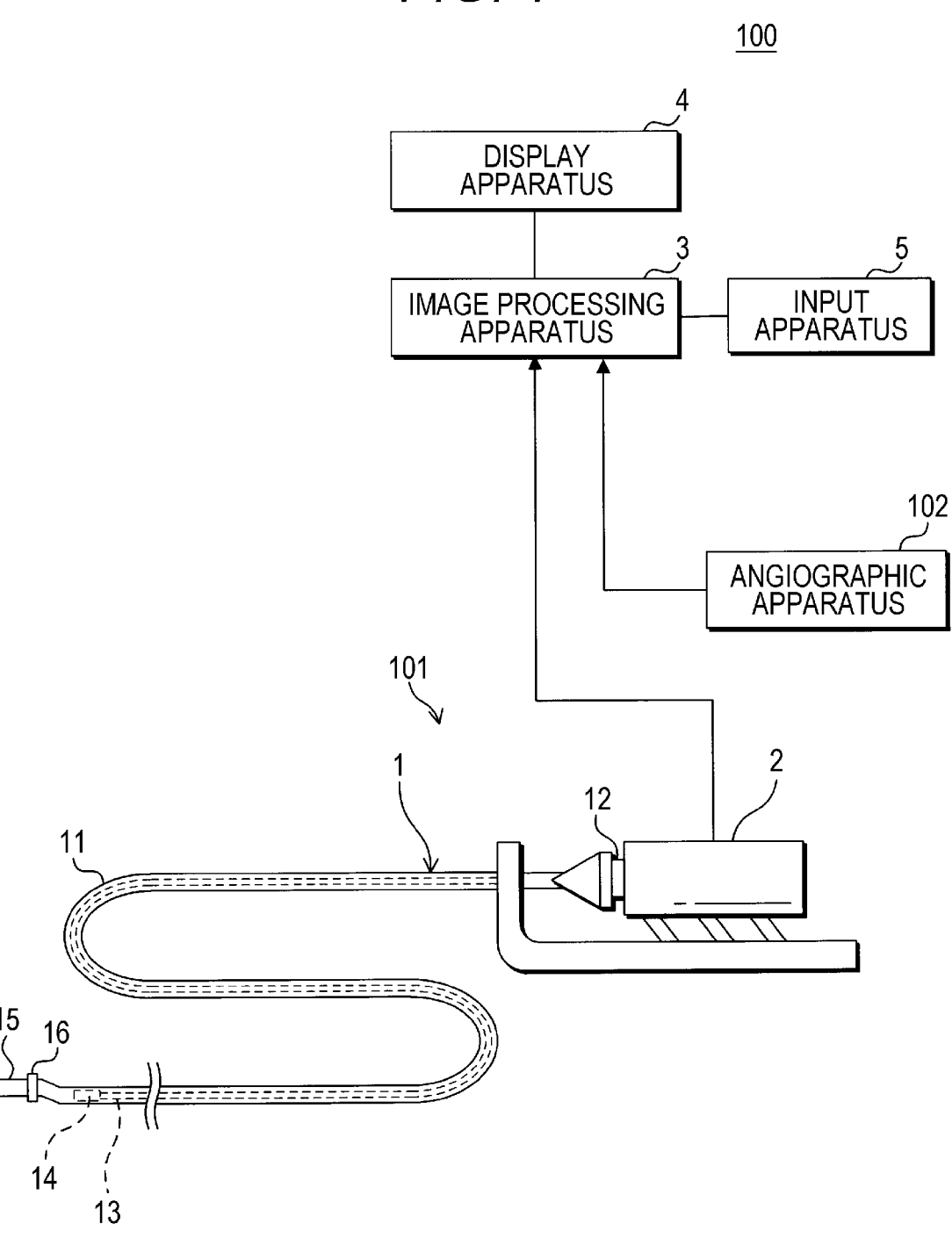
FIG. 1 is an explanatory view illustrating a configuration example of an image diagnosis device.

Set forth below with reference to the accompanying drawings is a detailed description of embodiments of a computer program, an image processing method, and an image processing device. In the drawings, similar components are denoted by the same reference signs, and the detailed description of the similar components will be appropriately omitted.

First Embodiment

FIG. 1 is an explanatory view illustrating a configuration example of an image diagnosis device 100. The image diagnosis device 100 according to the present embodiment includes an intravascular ultrasound inspection apparatus 101, an angiographic apparatus 102, an image processing apparatus (information processing apparatus) 3, a display apparatus 4, and an input apparatus 5. The image diagnosis device 100 is a device that images a luminal organ of a subject. Although the present embodiment will be described using an example of cardiac catheter treatment that is treatment within blood vessels, luminal organs that are catheter treatment targets are not limited to blood vessels and may be other luminal organs such as a bile duct, a pancreatic duct, a bronchus, and an intestine.

The intravascular ultrasound inspection apparatus 101 is an apparatus (or device) that generates an intra vascular ultrasound (IVUS) image (medical image) including an ultrasound tomographic image that is a cross section of a blood vessel of a subject by, for example, an IVUS method, and performs ultrasound inspection and diagnosis in the blood vessel. The intravascular ultrasound inspection apparatus 101 includes a catheter 1 and a motor drive unit (MDU) 2.

The catheter 1 is an image diagnosis catheter for obtaining an ultrasound tomographic image of a blood vessel by the IVUS method. The ultrasound tomographic image is an example of a catheter image generated using the catheter 1. The catheter 1 can include a probe 11 and a connector portion 12 disposed at an end portion of the probe 11. The probe 11 is connected to the MDU 2 via the connector portion 12. A shaft 13 is inserted into the probe 11. A sensor unit 14 is connected to a distal end side of the shaft 13.

The sensor unit 14, which is an ultrasonic transducer, transmits an ultrasound wave based on a pulse signal in the blood vessel and receives a reflected wave reflected by a biological tissue of the blood vessel or medical equipment. The sensor unit 14 and the shaft 13 can advance and retreat inside the probe 11 and can rotate in a circumferential direction. The sensor unit 14 and the shaft 13 rotate about a central axis of the shaft 13 as a rotation axis.

A guide wire insertion portion 15 through which a guide wire can be inserted is provided at a distal end of the probe 11. The guide wire insertion portion 15 constitutes a guide wire lumen, receives a guide wire inserted in advance into the blood vessel, and guides the probe 11 to an affected part by the guide wire. A center line of a tube portion in the guide wire lumen is separated from a center line of a tube portion of the probe 11 by a predetermined length.

The catheter 1 can also include a marker 16 that does not transmit X-rays in order to determine a positional relationship between the IVUS image obtained by the intravascular ultrasound inspection apparatus 101 and the angiographic image obtained by the angiographic apparatus 102. In the example of FIG. 1, the marker 16 is provided at a distal end of the probe 11. If the catheter 1 configured as described above is imaged with X-rays, an angiographic image that is a fluoroscopic image including an image of the marker 16 is obtained. Note that a position where the marker 16 is provided is an example, and the marker 16 may be provided on the shaft 13 or may be provided at a position other than the distal end of the probe 11.

The MDU 2 is a drive apparatus to which the catheter 1 is detachably attached, and controls operation of the catheter 1 inserted into the blood vessel by driving a built-in motor according to operation of the user. The MDU 2 performs pull-back operation of rotating the shaft 13 and the sensor unit 14 in the circumferential direction while pulling the shaft 13 and the sensor unit 14 toward the MDU 2 at constant speed. The sensor unit 14 continuously scans inside of the blood vessel at predetermined time intervals while rotating while moving from a distal end side to a proximal end side by the pull-back operation and outputs reflected wave data of the detected ultrasound wave to the image processing apparatus 3.

The image processing apparatus 3 is a processing apparatus that generates the IVUS image obtained by imaging the blood vessel on the basis of the reflected wave data output from the probe 11 of the catheter 1. The image processing apparatus 3 generates an image of one frame for each rotation of the sensor unit 14. The generated image is a transverse tomographic image centered on the probe 11 and substantially perpendicular to the probe 11. The sensor unit 14 scans while moving in the blood vessel, and thus, an image of one frame is generated at each position rotated by one rotation within the moving range (one pull-back range). In other words, images of a plurality of frames are generated within the moving range. The image processing apparatus 3 displays the generated ultrasound tomographic image on the display apparatus 4 and receives inputs of various setting values when performing an inspection via the input apparatus 5.

The catheter 1 may be a catheter for generating an optical tomographic image, such as for optical coherence tomography (OCT) or optical frequency domain imaging (OFDI) that generates an optical tomographic image using near-infrared light. In this case, the sensor unit 14 is a transmission/reception unit that emits near-infrared light and receives reflected light. The catheter 1 may include the sensor unit 14 of both an ultrasonic transducer and a transmission/reception unit for OCT or OFDI and may be for generating a medical image including both an ultrasound tomographic image and an optical tomographic image.

The angiographic apparatus 102 is an imaging apparatus that images a blood vessel from outside the patient's body using X-rays while injecting a contrast medium into the blood vessel of the patient and obtains an angiographic image (medical image) that is a fluoroscopic image of the blood vessel. The angiographic apparatus 102 includes an X-ray source and an X-ray sensor and images a fluoroscopic image of a patient by the X-ray sensor receiving X-rays emitted from the X-ray source. The angiographic apparatus 102 outputs an angiographic image obtained by imaging to the image processing apparatus 3.

In the present embodiment, the angiographic apparatus 102 that mainly captures a two-dimensional angiographic image will be described as an example, but there is no particular limitation as long as it is an apparatus that images a luminal organ of the patient and the catheter 1 from different directions outside the living body. For example, three-dimensional CT angiography, magnetic resonance imaging (MRI) image may be used.

The display apparatus 4 can be, for example, a liquid crystal display, an organic electro luminescence (EL) display, or the like, and the input apparatus 5 is, for example, a keyboard, a mouse, a trackball, a microphone, or the like. The display apparatus 4 and the input apparatus 5 may be integrally assembled or combined to constitute a touch panel. Further, the input apparatus 5 and the image processing apparatus 3 may be integrally constituted or formed as a single unit. Furthermore, the input apparatus 5 may be a sensor that receives a gesture input, a line-of-sight input, or the like.

Figure 2:
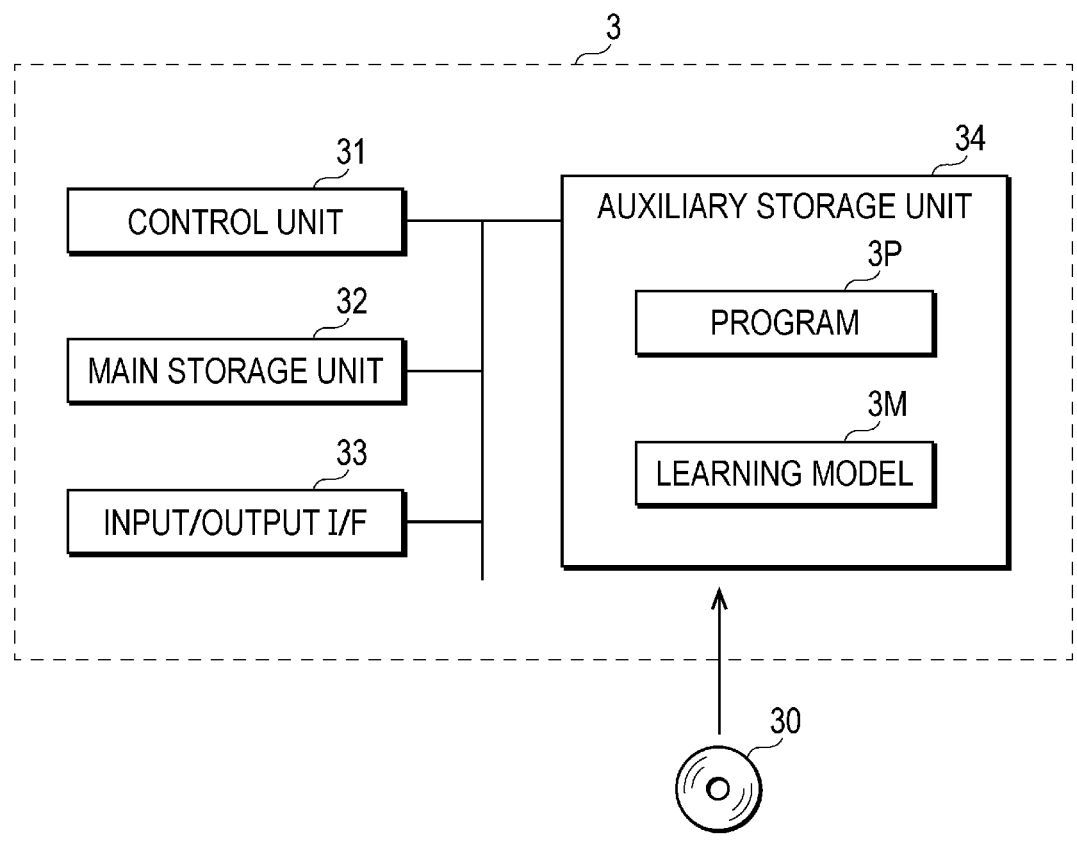
FIG. 2 is a block diagram illustrating a configuration example of an image processing device.

FIG. 2 is a block diagram illustrating a configuration example of the image processing apparatus 3. The image processing apparatus 3, which is a computer, can include a control unit 31, a main storage unit 32, an input/output I/F 33, and an auxiliary storage unit 34.

The image processing apparatus 3 may be a multi-computer including a plurality of computers. In addition, the image processing apparatus 3 may be a server client system, a cloud server, or virtual machine virtually constructed by software. In the following description, it is assumed that the image processing apparatus 3 is one computer.

The control unit 31 can be, for example, constituted using one or a plurality of arithmetic processing units such as a central processing unit (CPU), a micro-processing unit (MPU), a graphics processing unit (GPU), a general-purpose computing on graphics processing unit (GPGPU), and a tensor processing unit (TPU). The control unit 31 is connected to each hardware unit constituting the image processing apparatus 3 via a bus.

The main storage unit 32, which is a temporary storage area such as a static random access memory (SRAM), a dynamic random access memory (DRAM), or a flash memory, temporarily stores data necessary for the control unit 31 to execute arithmetic processing.

The input/output I/F 33 is an interface to which the intravascular ultrasound inspection apparatus 101 and the angiographic apparatus 102, the display apparatus 4, and the input apparatus 5 are connected. The control unit 31 acquires an IVUS image or an angiographic image via the input/output I/F 33. In addition, the control unit 31 outputs a medical image signal of the IVUS image or the angiographic image to the display apparatus 4 via the input/output I/F 33, thereby displaying the medical image on the display apparatus 4. Furthermore, the control unit 31 receives information input to the input apparatus 5 via the input/output I/F 33.

The auxiliary storage unit 34 can be, for example, a storage apparatus such as a hard disk, an electrically erasable programmable ROM (EEPROM), or a flash memory. The auxiliary storage unit 34 stores a program 3P to be executed by the control unit 31 and various data necessary for processing of the control unit 31. In addition, the auxiliary storage unit 34 stores a learning model 3M. Details of the learning model 3M will be described later.

Note that the auxiliary storage unit 34 may be an external storage apparatus connected to the image processing apparatus 3. The program 3P may be written in the auxiliary storage unit 34 at a manufacturing stage of the image processing apparatus 3, or a program to be distributed by a remote server apparatus may be acquired by the image processing apparatus 3 through communication and stored in the auxiliary storage unit 34. The program 3P may be recorded in a readable manner on a recording medium 30 such as a magnetic disk, an optical disk and a semiconductor memory, or a reading unit may read the program from the recording medium 30 and store the program in the auxiliary storage unit 34.

The control unit 31 reads and executes the program 3P stored in the auxiliary storage unit 34 to execute processing of acquiring the IVUS image generated by the image diagnosis apparatus 100, specifying a direction of interest for the IVUS image, and displaying the IVUS image associated with information indicating the specified direction of interest.

The direction of interest indicates a direction of a site of interest in which a doctor, or the like, is interested. The doctor, or the like, grasps an imaging direction of the IVUS image with respect to the subject on the basis of the direction of interest in the IVUS image. Hereinafter, an example in which the site of interest is the epicardium and the direction of interest is the direction of the epicardium will be described. For example, in cardiac catheter treatment, it is important to correctly grasp the direction of the epicardium of the subject in order to predict cardiac tamponade, which is a serious complication. In other words, it is important to correctly grasp the direction of the epicardium with respect to the IVUS image. However, the direction of the IVUS image changes as needed according to an insertion state of the catheter 1 in the blood vessel. It takes skill to correctly grasp the direction of the epicardium from information drawn in the IVUS image, and it is not relatively easy for an inexperienced doctor. In addition, there is a case where information from which the direction of the epicardium can be specified is not drawn in the IVUS image depending on imaging conditions, in which case, it is further difficult to grasp the direction of the epicardium with respect to such an IVUS image. In the present embodiment, the direction of the epicardium is specified by the image processing apparatus 3, and the IVUS image associated with information indicating the specified direction of the epicardium is provided, so that a doctor, or the like, can relatively easily recognize the direction of the epicardium.

A method of specifying a direction of interest of the IVUS image in the present embodiment will be described. The control unit 31 of the image processing apparatus 3 detects a merkmal (anatomical characteristic) included in the IVUS image using the learning model 3M and specifies the direction of interest of the IVUS image on the basis of the detection result. The merkmal is information serving as a mark for specifying the direction of interest of the IVUS image. For example, the merkmal can be, for example, a site of interest, a shape of a luminal organ into which the catheter 1 is inserted, a side branch structure, an organ such as a heart adjacent to the luminal organ, a luminal organ around the luminal organ, a lesion, and the like. In a case where the direction of interest is the direction of the epicardium, the merkmal can include, for example, the epicardium directly indicating the direction of the epicardium, a blood vessel of a side branch indirectly indicating the direction of the epicardium, a vein, trance-thoracic sinus, Triangle of Brocq-Mouchet, a myocardial bridge, a calcified lesion, a guide wire, and the like.

Figure 3:
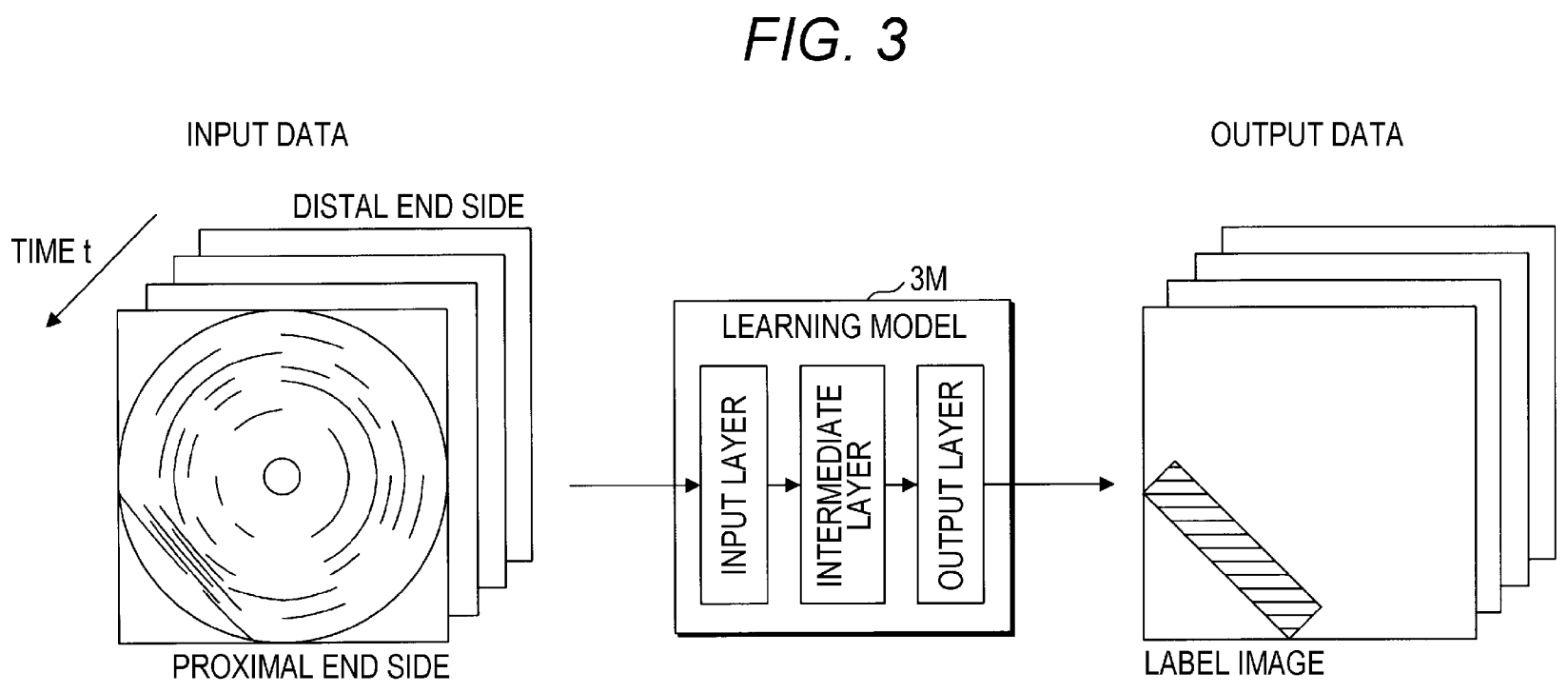

FIG. 3 is an explanatory view illustrating outline of the learning model 3M. The learning model 3M is a model that receives the IVUS image as an input and outputs information regarding a predetermined object (merkmal) included in the IVUS image. Specifically, the learning model 3M receives, as an input, the IVUS images of a plurality of frames continuous along a longitudinal direction of the blood vessel according to scanning of the catheter 1. The learning model 3M recognizes the merkmals in the IVUS images of the respective frames continuous along a time axis t.

The learning model 3M can be, for example, a learned convolutional neural network (CNN) by deep learning. The learning model 3M recognizes whether or not each pixel in an input image is a pixel corresponding to an object area on a pixel basis by an image recognition technology using semantic segmentation. The learning model 3M includes an input layer to which the IVUS image is input, an intermediate layer that extracts and restores a feature amount of the image, and an output layer that outputs information indicating a position, a range, and a type of an object included in the IVUS image. The learning model 3M can be, for example, U-Net.

The input layer of the learning model 3M includes a plurality of nodes that receives an input of a pixel value of each pixel included in the IVUS image and passes the input pixel value to the intermediate layer. The intermediate layer includes a convolution layer (CONV layer) and a deconvolution layer (DECONV layer). The convolution layer is a layer that dimensionally compresses image data. A feature amount of the object is extracted by the dimension compression. The deconvolution layer executes deconvolution processing to restore the original dimension. By the restoration processing in the deconvolution layer, a label image indicating whether or not each pixel of the IVUS image is an object by a pixel value corresponding to a type of the object is generated. The output layer includes a plurality of nodes that output label images. The label image can be, for example, an image in which a pixel corresponding to a first merkmal (epicardium) is class "1", a pixel corresponding to a second merkmal (side branch) is class "2", a pixel corresponding to a third merkmal (vein) is class "3", . . . , and a pixel corresponding to another image is class "0".

The learning model 3M may further include a medical image other than the IVUS image in an input element. The other medical image may include, for example, an optical tomographic image or an angiographic image captured at the same time as the IVUS image. In addition, the learning model 3M may include, as an input element, information regarding a luminal organ into which the catheter 1 is inserted. The information regarding the luminal organ may include, for example, names of blood vessels such as the right coronary artery, the left coronary artery, and the left anterior descending artery (LAD), numbers for identifying the blood vessels (AHA classification), and the like. By inputting these to the learning model 3M as input elements, it is possible to recognize the merkmal in consideration of information other than the IVUS image, so that it is possible to improve recognition accuracy.

The learning model 3M can be generated by preparing training data in which an IVUS image including an object (merkmal) is associated with a label image indicating a position, a range, and a type of each object and causing an unlearned neural network to perform machine learning using the training data. Specifically, the control unit 31 inputs a plurality of IVUS images included in the training data to the input layer of the neural network model before learning, performs arithmetic processing in the intermediate layer, and acquires an image output from the output layer. Then, the control unit 31 compares the image output from the output layer with the label image included in the training data and optimizes parameters to be used for the arithmetic processing in the intermediate layer so that the image output from the output layer approaches the label image. The parameters can be, for example, a weight (coupling coefficient) between neurons. A parameter optimization method is not particularly limited, but for example, the control unit 31 optimizes various parameters using an error back propagation method. A correct label may be set to a position of the merkmal in the training data, for which, for example, a doctor having specialized knowledge has made determination.

According to the learning model 3M learned in this way, as illustrated in FIG. 3, by inputting the IVUS image to the learning model 3M, a label image indicating various types of merkmal in units of pixels can be obtained.

Although the example in which the learning model 3M is the CNN has been described above, the configuration of the learning model 3M is not limited as long as it can recognize the merkmal included in the IVUS image. The learning model 3M may be, for example, R-CNN, Mask R-CNN, YOLO (You Only Look Once), or the like, or may be a model constructed by another learning algorithm such as support vector machine not using a neural network or a regression tree.

The control unit 31 of the image processing apparatus 3 specifies the direction of interest in the IVUS image using the detection result of the merkmal. In a case where the detected merkmal is the epicardium, that is, the detected merkmal is the site of interest, the control unit 31 directly specifies the direction of the detected merkmal as the direction of the epicardium. In a case where the detected merkmal is not the epicardium, that is, the detected merkmal is not the site of interest, the control unit 31 indirectly specifies the direction of the epicardium from the direction of another merkmal on the basis of a positional relationship between the epicardium and a merkmal (hereinafter, referred to as another merkmal) which is not the epicardium stored in advance. The direction of the epicardium is indicated using, for example, an angle in a case where a 0:00 direction is set as a reference (0 degrees) with respect to a substantially circular IVUS image.

For example, the control unit 31 stores in advance a rotation angle with respect to the other merkmal on the basis of the positional relationship between the other merkmal and the epicardium. The rotation angle is an angle at which the probe 11 is rotated in a circumferential direction with respect to the center of the probe 11 in the IVUS image in order to calculate the direction of the epicardium from the direction of the other merkmal. The control unit 31 specifies, as the direction of the epicardium, a direction rotated by a predetermined angle from the other merkmal on the basis of the detected other merkmal. For example, a case where a blood vessel of a side branch branched from a blood vessel into which the catheter 1 is inserted is detected as another merkmal will be described. The control unit 31 calculates the direction of the epicardium by rotating the direction of the blood vessel of the side branch by a predetermined angle on the basis of a correspondence relationship between the blood vessel of the side branch stored in advance and a rotation angle defined by a positional relationship between the blood vessel and the blood vessel of the side branch.

The control unit 31 may use information other than the IVUS image in specifying the direction of the epicardium. The information other than the IVUS image may include, for example, the optical tomographic image captured at the same time as the IVUS image, the angiographic image, information regarding the luminal organ into which the catheter 1 is inserted, and the like. The information regarding the luminal organ can be, for example, names of blood vessels such as the right coronary artery, the left coronary artery, and the LAD, numbers for identifying the blood vessels (AHA classification), and the like. For example, a case where a guide wire is detected as another merkmal will be described. The angiographic image captured at the same time as the IVUS image can include images of the blood vessel, the catheter 1 (marker 16), and the guide wire. The control unit 31 specifies a positional relationship between the IVUS image and the angiographic image (the position and direction of the IVUS image with respect to the angiographic image) on the basis of the direction of the guide wire in the IVUS image and the positions of the blood vessel, the catheter 1 (marker 16), and the guide wire in the angiographic image. The control unit 31 specifies the direction of the IVUS image with respect to the subject on the basis of the specified positional relationship and an imaging direction of the angiographic image with respect to the subject. The control unit 31 specifies the direction of the epicardium with respect to the IVUS image on the basis of the specified direction of the IVUS image.

In this manner, the control unit 31 directly or indirectly specifies the direction (direction of interest) of the epicardium with respect to the IVUS image on the basis of the merkmal included in the IVUS image.

Next, the control unit 31 removes an outlier from the specified direction of the epicardium. Specifically, the control unit 31 detects and removes a direction (outlier) of the epicardium deviated from most of the directions of the epicardium on the basis of the directions of the epicardium in a plurality of IVUS images in time series continuous along the longitudinal direction of the blood vessel. The outlier detection method is not limited. As an example, the control unit 31 derives a deviation between a direction (angle) of the epicardium in each IVUS image (each frame) and a moving average of time-series data of the direction (angle) of the epicardium and detects a direction of the epicardium in which an absolute value of the derived deviation is equal to or greater than a threshold as an outlier. The control unit 31 removes the detected outlier from the specification result.

Furthermore, the control unit 31 estimates the direction of the epicardium with respect to the IVUS image in which the merkmal is not detected. Specifically, the control unit 31 interpolates a discontinuous portion where the direction of the epicardium is not obtained by a predetermined interpolation method (such as, for example, spline interpolation and linear interpolation) on the basis of the time-series data of the direction (angle) of the epicardium from which the outlier is removed. As a result, the control unit 31 acquires the direction of the epicardium with respect to the IVUS image in which the merkmal is not detected and the direction of the epicardium is not specified. The IVUS image acquired using the catheter 1 does not necessarily include the merkmal, and thus, the direction of the epicardium can be given to all the IVUS images by performing the interpolation processing using previous and subsequent frames. The interpolation processing may be similarly performed not only on the IVUS image in which the merkmal is not detected but also on the IVUS image from which the specification result is removed as an outlier.

FIG. 4 is a flowchart illustrating an example of processing procedure to be executed by the image processing apparatus 3. The control unit 31 of the image processing apparatus 3 executes the following processing according to the program 3P. For example, the control unit 31 may perform the following processing in real time every time a medical image is output via the intravascular ultrasound inspection apparatus 101 or may perform processing afterwards at any timing on the basis of the recorded medical image.

The control unit 31 of the image processing apparatus 3 acquires a medical image including an IVUS image via the intravascular ultrasound inspection apparatus 101 (S11). Specifically, the control unit 31 acquires the IVUS image generated on the basis of a signal of a reflected wave of an ultrasound wave acquired via the intravascular ultrasound inspection apparatus 101. The control unit 31 functions as an acquisition unit that acquires a medical image obtained by imaging a blood vessel. In this case, the control unit 31 may acquire an optical tomographic image together with the IVUS image or may acquire an angiographic image via the angiographic apparatus 102.

The control unit 31 inputs the acquired IVUS image to the learning model 3M as input data (S12). The control unit 31 acquires a label image indicating the position, range, and type of the merkmal output from the learning model 3M (S13). The control unit 31 determines whether or not the merkmal is an epicardium, that is, a site of interest (S14). Note that the control unit 31 may acquire and store the site of interest by receiving registration of the site of interest in advance, for example.

In a case where it is determined that the merkmal is not the epicardium (S14: No), the control unit 31 specifies a direction (angle) of the epicardium with respect to the IVUS image on the basis of the detected positional relationship between the merkmal (another merkmal) which is not the epicardium and the epicardium (S15), and the processing proceeds to S17. For example, the control unit 31 specifies a direction rotated from the direction of the other merkmal by a predetermined angle as the direction of the epicardium on the basis of the detected other merkmal with reference to a correspondence relationship between the direction of the other merkmal and the direction of the epicardium stored in advance. In this case, the control unit 31 may specify the direction of the epicardium using information other than the IVUS image, for example, the optical tomographic image, the angiographic image, or information regarding the luminal organ into which the catheter 1 is inserted.

In a case where it is determined that merkmal is the epicardium (S14: Yes), the control unit 31 specifies the direction of the epicardium with respect to the IVUS image according to the detected epicardium (S16). The control unit

31 specifies, for example, an angle passing through the circumferential center of the detected epicardium as the direction of the epicardium according to the position and the range of the detected epicardium.

The control unit 31 determines whether or not the merkmal detection processing for all the acquired IVUS images has been completed (S17). In a case where it is determined that the detection processing for all the IVUS images has not been completed (S17: No), the processing of the control unit 31 returns to S12, and the control unit 31 waits until the detection processing for all the IVUS images is completed.

In a case where it is determined that the detection processing for all the IVUS images has been completed (S17: Yes), the control unit 31 detects an outlier in the specified direction of the epicardium on the basis of each detection result (S18). Specifically, the control unit 31 derives a deviation between the direction of the epicardium in each IVUS image (each frame) and the moving average of the time-series data in the direction of the epicardium. The control unit 31 detects the direction (outlier) of the epicardium in which the absolute value of the calculated deviation is equal to or greater than a threshold by determining a magnitude relationship between the absolute value of each calculated deviation and the threshold set in advance. The control unit 31 removes the detected outlier from the specification result regarding the direction of the epicardium, that is, the time-series data in the direction of the epicardium (S19).

The control unit 31 interpolates a discontinuous portion in which the direction of the epicardium is not obtained by a predetermined interpolation method (for example, spline interpolation) on the basis of the time-series data of the direction of the epicardium from which the outlier is removed (S20). The control unit 31 specifies the direction of the epicardium related to the IVUS image from which the direction of the epicardium has not been obtained according to the interpolation result (S21). The IVUS image in which the direction of the epicardium has not been obtained includes the IVUS image in which the merkmal is not detected and the IVUS image from which the specification result is removed as the outlier. As a result, the direction of the epicardium is specified for all IVUS images. The control unit 31 functions as a specifying unit that specifies the direction of the epicardium with respect to the IVUS image.

The control unit 31 generates screen information for displaying the IVUS image corresponding to each specified direction of the epicardium (S22). Specifically, the control unit 31 generates screen information that displays the specified direction of each epicardium and the IVUS image in association with each other, or screen information that displays the IVUS image subjected to image processing on the basis of the specified direction of each epicardium. The control unit 31 causes the display apparatus 4 to display the screen 40 on the basis of the generated screen information (S23) and ends the series of processing. The control unit 31 functions as a display unit that displays the direction of the epicardium and the IVUS image in association with each other or displays the IVUS image subjected to image processing on the basis of the direction of the epicardium.

Figure 5:
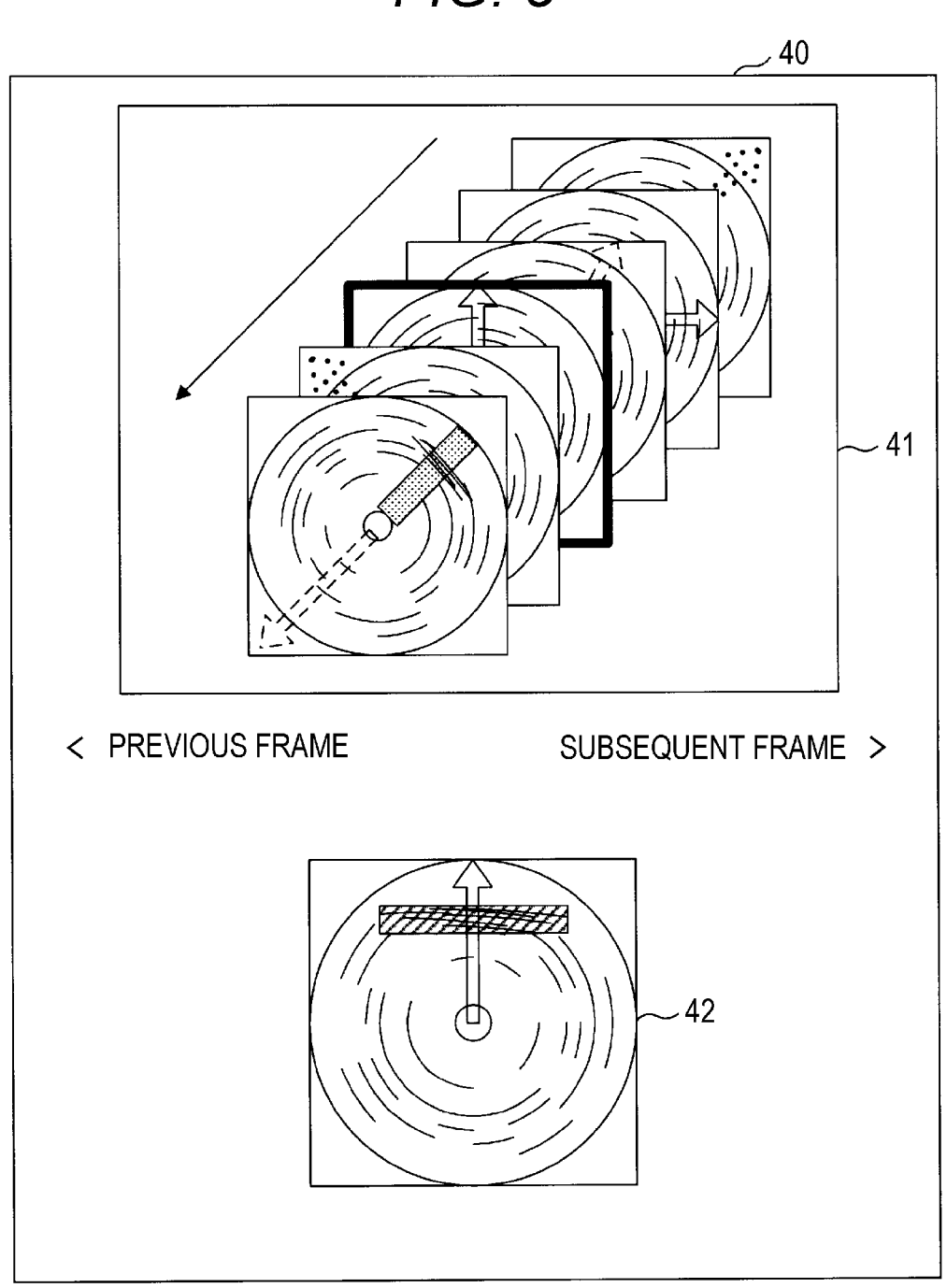
FIG. 5 is a schematic view illustrating an example of a screen to be displayed on a display device.

FIG. 5 is a schematic view illustrating an example of a screen 40 displayed on the display apparatus 4. The screen 40 includes an entire image display unit 41 that displays a plurality of IVUS images corresponding to a plurality of frames arranged in chronological order, and a selected image display unit 42 that displays an IVUS image selected by a doctor, or the like, among the plurality of IVUS images. The selected image display unit 42 displays any IVUS image and information indicating the direction of the epicardium with respect to the IVUS image in association with each other. In the example illustrated in FIG. 5, the selected image display unit 42 superimposes and displays a graphic object (arrow) indicating the direction of the epicardium on the IVUS image. Further, the selected image display unit 42 superimposes and displays the merkmal detected from the IVUS image on the IVUS image.

The control unit 31 of the image processing apparatus 3 acquires, for each of the plurality of IVUS images acquired by one pull-back operation, the detection result (label image) of the merkmal by the learning model 3M and the specification result of the direction of the epicardium in association with each other. The control unit 31 processes the label image output from the learning model 3M for each IVUS image into a translucent mask and superimposes and displays the translucent mask on the original IVUS image. In this case, the control unit 31 may change a display mode of each of the merkmal regions according to the type of merkmal, such as changing display color of the mask according to the type of merkmal. In the example illustrated in FIG. 5, hatching different according to the merkmal is used for display.

In addition, the control unit 31 generates a figure object extending from the center of the IVUS image toward the epicardium according to the direction (angle) of the epicardium with respect to each IVUS image and superimposes and displays the figure object on the original IVUS image. In this case, the control unit 31 may change a display mode of each figure object according to specified content of the direction of the epicardium, such as changing a line type and display color of the figure object according to the specified content of the direction of the epicardium. The specified content of the direction of the epicardium can be, for example, direct specification using the epicardium as the merkmal, indirect specification using a material other than the epicardium as the merkmal, and indirect specification by interpolation using another frame. In the example illustrated in FIG. 5, the specified content of the direction of the epicardium is displayed in an identifiable manner using three types of line types of a solid line, a dashed line, and a dotted line. In FIG. 5, a solid arrow indicates the direction of interest in the IVUS image in which the epicardium is detected as the merkmal. In FIG. 5, a dashed arrow indicates the direction of interest in the IVUS image in which a portion other than the epicardium is detected as the merkmal. In FIG. 5, a dotted arrow indicates the direction of interest in the IVUS image in which the direction of interest is specified by interpolation.

The control unit 31 performs the above-described processing on all the acquired IVUS images and arranges the IVUS images in which the directions of the merkmal and the epicardium are associated with each other in chronological order and displays the images on the entire image display unit 41. The control unit 31 receives selection of any IVUS image among the IVUS images displayed on the entire image display unit 41 via, for example, the input apparatus 5, and displays the IVUS image corresponding to the selection on the selected image display unit 42.

As described above, the image processing apparatus 3 provides the screen 40 indicating the direction of the epicardium with respect to each IVUS image to the doctor, or the like, via the display apparatus 4. The doctor, or the like, can relatively easily grasp the direction of the epicardium with respect to each IVUS image on the screen 40. In addition, the specified content of the direction of the merkmal and the epicardium are displayed in an identifiable manner, so that the doctor, or the like, can estimate detection accuracy of the merkmal with respect to the IVUS image or specification accuracy of the direction of the epicardium and perform diagnosis in consideration of the estimation result.

The screen 40 illustrated in FIG. 5 is an example, and the display content is not limited to the example of FIG. 5. The screen 40 may display the medical image acquired in addition to the IVUS image, such as the OCT image or the angiographic image, for example. Furthermore, in a case where information other than the IVUS image, such as the optical tomographic image, the angiographic image, or information regarding the luminal organ into which the catheter 1 is inserted, is used, the control unit 31 may display these pieces of information on the screen 40 in association with the IVUS image.

A display mode of the direction of the epicardium is not limited. The direction of the epicardium may be displayed, for example, in the vicinity of the IVUS image. The direction of the epicardium may be displayed using a numerical value indicating an angle instead of or in addition to the graphical object.

The direction of the epicardium is not limited to the direction displayed in association with the IVUS image and may be indicated so that the direction can be recognized by applying image processing to the IVUS image. For example, the control unit 31 presents the direction of the epicardium by rotating each IVUS image on the basis of the direction of the epicardium in each IVUS image. The control unit 31 sets any one of a plurality of continuous IVUS images as a reference image and performs image processing of rotating the other IVUS image such that the direction of the epicardium in the reference image is synchronized with the direction of the epicardium in the other IVUS image on the basis of the direction of the epicardium in the reference image. For example, in a case where a first frame is the reference image, when the direction of the epicardium in the first frame is a 1:00 direction (i.e., position on a clock face) and the direction of the epicardium in a second frame is a 3:00 direction, the control unit 31 performs image processing of rotating the IVUS image of the second frame clockwise by 60 degrees. In this case, the control unit 31 may display information regarding image processing in association with the IVUS image, such as superimposing and displaying a rotation angle on the IVUS image. Note that the image processing method is not limited to rotating another IVUS image according to the reference image. For example, on the basis of the direction of the epicardium in each IVUS image, the control unit 31 may rotate each IVUS image so that the direction of the epicardium in each IVUS image coincides with the preset reference direction (for example, the 0:00 direction).

Note that the control unit 31 of the image processing apparatus 3 may relearn the learning model 3M with respect to the detection result of the merkmal. The control unit 31 receives an input for correcting the detection result of the merkmal from the doctor, or the like, and performs relearning on the basis of the input information. Specifically, the control unit 31 receives a correction input as to whether or not the position and type of the merkmal displayed as the detection result are correct on the screen 40 exemplified in FIG. 5, for example. Furthermore, in a case where the displayed position and type of the merkmal are erroneous, the control unit 31 receives an input of the correct position and type of the merkmal. In a case where the correction input is received, the control unit 31 performs relearning using an IVUS image labeled with the corrected detection result (position and type of the merkmal) as training data and updates the learning model 3M. Similarly, the control unit 31 may receive an input for correcting the result of specifying the direction of the epicardium from the doctor, or the like, with respect to the result of specifying the direction of the epicardium and may update a specification rule on the basis of the input information, which makes it possible to improve detection accuracy of the merkmal and specification accuracy of the direction of interest through the operation of the present system.

In the above description, an example of specifying the direction of the epicardium as the direction of interest has been described, but the present embodiment is not limited to the example of specifying the direction of the epicardium. For example, in a case where the catheter 1 is inserted into a lower limb blood vessel, the direction of interest may be a direction of a shin, a calf, or the like, and in a case where the catheter 1 is inserted into another luminal organ, the direction of interest may be a direction of an abdomen or a back.

The control unit 31 may store a plurality of learning models 3M and specification rules according to the site of interest (direction of interest) in the auxiliary storage unit 34. In this case, for example, the control unit 31 acquires the site of interest by receiving selection registration from the doctor, or the like, before examination, selects the learning model 3M and the specification rule according to the acquired site of interest and executes detection of the merkmal and the specification processing of the direction of interest using the selected learning model 3M and specification rule.

According to the present embodiment, the merkmal for specifying the direction of the epicardium with respect to the IVUS image is accurately estimated using the learning model 3M, and the direction of the epicardium is efficiently specified according to the estimation result. The specification result of the direction of the epicardium is displayed on the screen 40 in a visually easily recognizable manner, so that even a doctor, or the like, who is inexperienced in interpretation of the IVUS image can relatively easily grasp the direction of the epicardium and can relatively easily specify the direction of the epicardium with respect to each IVUS image. The doctor, or the like, can three-dimensionally integrate and intuitively grasp information acquired using a plurality of modalities, such as the IVUS image by the intravascular ultrasound inspection apparatus 101 and the angiographic image by the angiographic apparatus 102, for example, so that it is possible to suitably support diagnosis by the doctor, or the like.

In addition, according to the present embodiment, the direction of interest is specified by different procedure depending on whether or not the merkmal is the site of interest, so that the direction of interest can be accurately specified depending on the type of the merkmal. Accuracy of the specification result of the direction of interest is improved by removing outliers. Furthermore, by the interpolation processing using the previous and subsequent frame images, the direction of interest can also be suitably specified for the IVUS image in which the merkmal is not detected.

Second Embodiment

The second embodiment is different from the first embodiment in that the direction of interest is directly specified by the learning model. Hereinafter, differences from the first embodiment will be mainly described, and components common to the first embodiment will be denoted by the same reference numerals, and detailed description of the components common to the first embodiment will be omitted.

Figure 6:
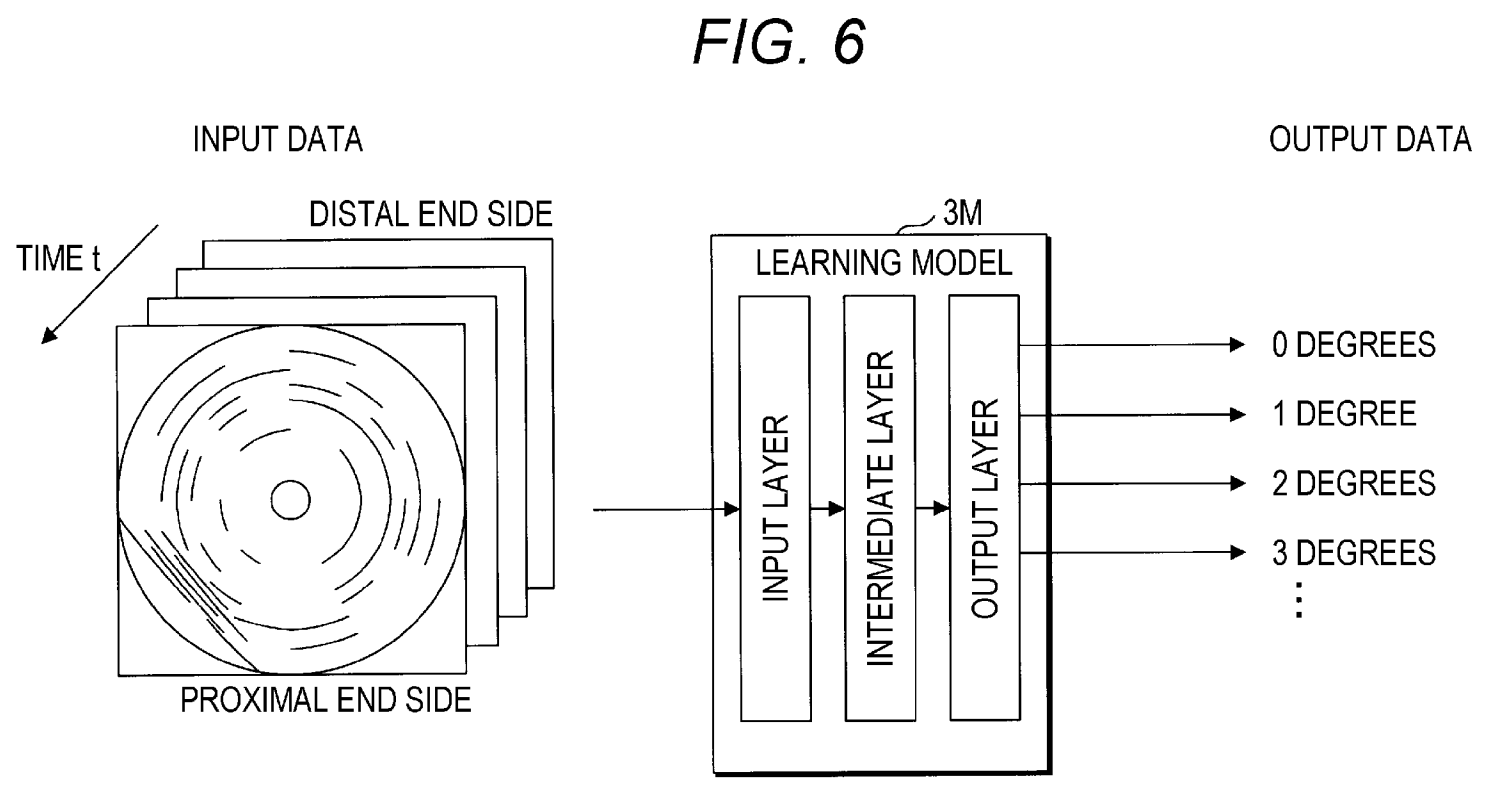

The control unit 31 of the image processing apparatus 3 specifies the direction of interest in the IVUS image using the learning model 3M stored in the auxiliary storage unit 34. FIG. 6 is an explanatory view for explaining outline of the learning model 3M in the second embodiment. The learning model 3M in the second embodiment is a model that receives the IVUS image as an input and outputs information indicating the direction of interest (for example, the direction of the epicardium) in the IVUS image. Specifically, the learning model 3M receives, as an input, the IVUS images of a plurality of frames continuous along a longitudinal direction of the blood vessel according to scanning of the catheter 1. The learning model 3M identifies the direction of interest in the IVUS image of each successive frame along the time axis t.

The learning model 3M can be, for example, a learned convolutional neural network by deep learning. The learning model 3M includes an input layer to which the IVUS image is input, an intermediate layer that extracts a feature amount of the image, and an output layer that outputs information indicating the direction of interest in the IVUS image. The intermediate layer may include a convolution layer, a pooling layer, a fully connected layer, and the like.

The input layer of the learning model 3M includes a plurality of nodes that receives an input of a pixel value of each pixel included in the IVUS image and passes the input pixel value to the intermediate layer. The intermediate layer includes a plurality of nodes that extracts a feature amount of input data, and outputs the extracted feature amount using various parameters.

The output layer has a plurality of nodes each corresponding to a set angle (for example, 0 degrees, 1 degree, 2 degrees, . . . ) of the direction of interest and outputs accuracy for each direction of interest as a score. The control unit 31 can set the direction of interest having the highest score or the direction of interest having a score equal to or greater than a threshold as an output value of the output layer. Note that the output layer may have one output node that outputs an angle of the direction of interest with the highest accuracy, instead of having a plurality of output nodes that outputs accuracy with respect to the angle of each direction of interest.

The learning model 3M can be generated by preparing training data in which the IVUS image and the label indicating each direction of interest are associated with each other and causing an unlearned neural network to perform machine learning using the training data. Specifically, the control unit 31 inputs a plurality of IVUS images included in the training data to the input layer of the neural network model before learning, performs arithmetic processing in the intermediate layer and acquires the direction of interest output from the output layer. Then, the control unit 31 compares the direction of interest output from the output layer with the direction of interest included in the training data and optimizes parameters to be used for the arithmetic processing in the intermediate layer so that the direction of interest output from the output layer approaches the direction of interest included in the training data. The parameters can be, for example, a weight (coupling coefficient) between neurons. A parameter optimization method is not particularly limited, but for example, the control unit 31 optimizes various parameters using an error back propagation method. A correct label may be set to the direction of interest in the training data, for which, for example, a doctor having specialized knowledge has made determination.

The learning model 3M may further include a medical image other than the IVUS image in an input element. The other medical image may include, for example, an optical tomographic image or an angiographic image captured at the same time as the IVUS image. In addition, the learning model 3M may include, as an input element, information regarding a luminal organ into which the catheter 1 is inserted. The information regarding the luminal organ may include, for example, names of blood vessels such as the right coronary artery, the left coronary artery, and the LAD, numbers for identifying the blood vessels (AHA classification), and the like. By inputting these as input elements to the learning model 3M, it is possible to specify the direction of interest in consideration of information other than the IVUS image, so that it is possible to improve the accuracy of the specified direction of interest.

Although the example in which the learning model 3M is the CNN has been described above, the configuration of the learning model 3M is not limited as long as the direction of interest in the IVUS image can be specified. For example, the learning model 3M may be a recurrent neural network (RNN) in a case where time-series data is acquired or may be a model constructed by another learning algorithm such as support vector machine not using a neural network or a regression tree.

Figure 7:
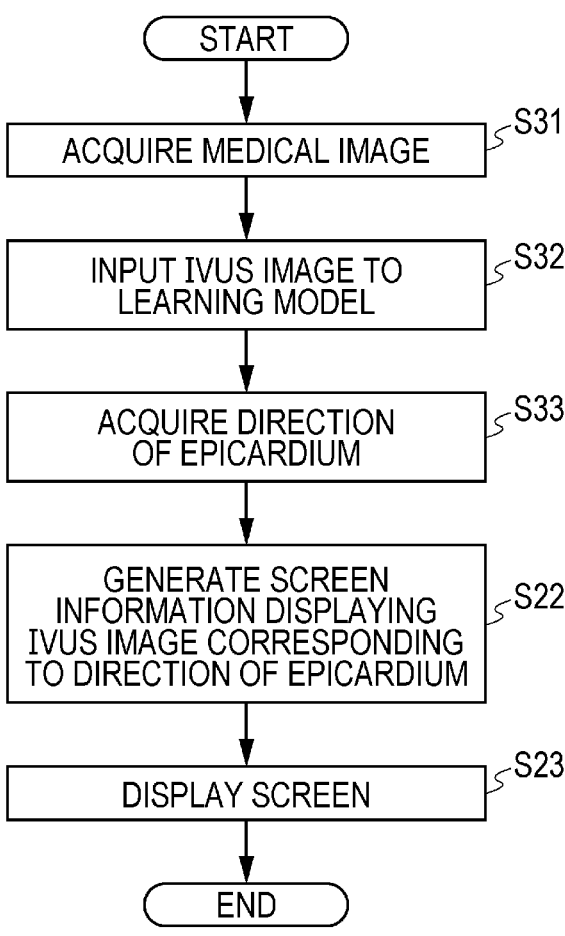
FIG. 7 is a flowchart illustrating an example of processing procedure to be executed by an image processing device according to a second embodiment.

FIG. 7 is a flowchart illustrating an example of processing procedure to be executed by the image processing apparatus 3 in the second embodiment. The control unit 31 of the image processing apparatus 3 executes the following processing according to the program 3P.

The control unit 31 of the image processing apparatus 3 acquires a medical image including the IVUS image via the intravascular ultrasound inspection apparatus 101 (S31). In this case, the control unit 31 may acquire an optical tomographic image together with the IVUS image or may acquire an angiographic image via the angiographic apparatus 102.

The control unit 31 inputs the acquired IVUS image to the learning model 3M as input data (S32). The control unit 31 specifies the direction of the epicardium with respect to the IVUS image by acquiring information indicating the direction of the epicardium output from the learning model 3M (S33). Thereafter, the control unit 31 outputs a screen displaying the IVUS image corresponding to the direction of the epicardium output from the learning model 3M by executing the processing of S22 to S23 illustrated in FIG. 4.

In the above-described processing, in a case where the result of specifying the direction of the epicardium by the learning model 3M cannot be obtained for any of the IVUS images, the control unit 31 may execute the interpolation processing of S20 to S21 illustrated in FIG. 4.

According to the present embodiment, it is possible to accurately estimate the direction of the epicardium with respect to the IVUS image using the learning model 3M.

In each of the above-described flowcharts, part or all of the processing to be executed by the image processing apparatus 3 may be executed by an external server (not illustrated) communicably connected to the image processing apparatus 3. In this case, a program and a learning model similar to the program 3P and the learning model 3M described above are stored in the storage unit of the external server. The external server acquires a medical image from the image processing apparatus 3 via a network such as a local area network (LAN) and the Internet. The external server executes processing similar to that of the image processing apparatus 3 of each embodiment on the basis of the acquired medical image and transmits a result of specifying the direction of the epicardium to the image processing apparatus 3. The image processing apparatus 3 acquires a result of specifying the direction of the epicardium transmitted from the external server, superimposes a graphic object indicating the direction of the epicardium on the IVUS image as illustrated in FIG. 5 and causes the display apparatus 4 to display the superimposed graphic object.

In the examples described in the foregoing embodiments, other embodiments can be implemented by combining all or some of the configurations described in the embodiments. In addition, the sequence described in each of the above embodiments is not limited, and each processing procedure may be executed in a changed order, or a plurality of kinds of processing may be executed in parallel.

The detailed description above describes embodiments of a program, an information processing method, and an information processing device. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A non-transitory computer-readable medium storing a computer program executed by a computer to execute a process comprising:

acquiring a medical image obtained by imaging a luminal organ using a catheter;

specifying a direction of interest indicating a direction of a site of interest with respect to the medical image on a basis of the acquired medical image, wherein the direction of interest comprises specifying a direction of an epicardium; and displaying information indicating the specified direction of interest and the medical image in association with each other or displaying the medical image subjected to image processing on a basis of the information indicating the direction of interest.

2. The computer-readable medium according to claim 1, wherein the direction of interest is specified by inputting the acquired medical image to a learning model that outputs the direction of interest for the medical image in a case where the medical image is input.

3. The computer-readable medium according to claim 1, further comprising:

detecting a merkmal included in the medical image;

specifying the direction of interest on a basis of the merkmal in a case where the detected merkmal is the site of interest; and specifying the direction of interest on a basis of a positional relationship between the merkmal and the site of interest in a case where the detected merkmal is not the site of interest.

4. The computer-readable medium according to claim 3, further comprising:

acquiring a second medical image including the merkmal;

specifying a positional relationship between the medical image and the second medical image on a basis of the merkmal included in the medical image and the merkmal included in the second medical image; and specifying the direction of interest on a basis of the specified positional relationship.

5. The computer-readable medium according to claim 1, further comprising:

specifying the direction of interest for each of a plurality of the medical images; and removing an outlier of the direction of interest specified on a basis of the direction of interest for each of the plurality of the medical images.

6. The computer-readable medium according to claim 1, further comprising:

specifying the direction of interest for each of a plurality of medical images; and specifying the direction of interest for a medical image for which the direction of interest is not specified by performing interpolation using the specified direction of interest for each of the plurality of the medical images.

7. The computer-readable medium according to claim 1, further comprising:

displaying an intravascular ultrasound (IVUS) corresponding to the direction of the epicardium.

8. An information processing method comprising:

acquiring a medical image obtained by imaging a luminal organ using a catheter;

specifying a direction of interest indicating a direction of a site of interest with respect to the medical image on a basis of the acquired medical image, wherein the direction of interest comprises specifying a direction of an epicardium; and displaying information indicating the specified direction of interest in association with the medical image or displaying the medical image subjected to image processing on a basis of the information indicating the direction of interest.

9. The method according to claim 8, wherein the direction of interest is specified by inputting the acquired medical image to a learning model that outputs the direction of interest for the medical image in a case where the medical image is input.

10. The method according to claim 8, further comprising:

detecting a merkmal included in the medical image;

specifying the direction of interest on a basis of the merkmal in a case where the detected merkmal is the site of interest; and specifying the direction of interest on a basis of a positional relationship between the merkmal and the site of interest in a case where the detected merkmal is not the site of interest.

11. The method according to claim 10, further comprising:

acquiring a second medical image including the merkmal;

specifying a positional relationship between the medical image and the second medical image on a basis of the merkmal included in the medical image and the merkmal included in the second medical image; and specifying the direction of interest on a basis of the specified positional relationship.

12. The method according to claim 8, further comprising:

specifying the direction of interest for each of a plurality of the medical images; and removing an outlier of the direction of interest specified on a basis of the direction of interest for each of the plurality of the medical images.

13. The method according to claim 8, further comprising:

specifying the direction of interest for each of a plurality of medical images; and specifying the direction of interest for a medical image for which the direction of interest is not specified by performing interpolation using the specified direction of interest for each of the plurality of the medical images.

14. An information processing device comprising:

a control unit configured to:

acquire a medical image obtained by imaging a luminal organ using a catheter;

specify a direction of interest indicating a direction of a site of interest with respect to the medical image on a basis of the medical image acquired by the acquisition unit, wherein the direction of interest comprises specifying a direction of an epicardium; and display information indicating the direction of interest specified by the specification unit in association with the medical image or displays the medical image subjected to image processing on a basis of the information indicating the direction of interest.

15. The image processing device according to claim 14, wherein the direction of interest is specified by inputting the acquired medical image to a learning model that outputs the direction of interest for the medical image in a case where the medical image is input.

16. The image processing device according to claim 14, wherein the control unit is further configured to:

detect a merkmal included in the medical image;

specify the direction of interest on a basis of the merkmal in a case where the detected merkmal is the site of interest; and specify the direction of interest on a basis of a positional relationship between the merkmal and the site of interest in a case where the detected merkmal is not the site of interest.

17. The image processing device according to claim 16, wherein the control unit is further configured to:

acquire a second medical image including the merkmal;

specify a positional relationship between the medical image and the second medical image on a basis of the merkmal included in the medical image and the merkmal included in the second medical image; and specify the direction of interest on a basis of the specified positional relationship.

18. The image processing device according to claim 14, wherein the control unit is further configured to:

specify the direction of interest for each of a plurality of the medical images; and remove an outlier of the direction of interest specified on a basis of the direction of interest for each of the plurality of the medical images.

19. The image processing device according to claim 14, wherein the control unit is further configured to:

specify the direction of interest for each of a plurality of medical images; and specify the direction of interest for a medical image for which the direction of interest is not specified by performing interpolation using the specified direction of interest for each of the plurality of the medical images.

* * * * *